US009597390B2

(12) United States Patent
Verheije et al.

(10) Patent No.: US 9,597,390 B2
(45) Date of Patent: Mar. 21, 2017

(54) INFECTIOUS BRONCHITIS VIRUS (IBV) SPIKE PROTEIN AS SUBUNIT VACCINE

(75) Inventors: Hélène Verheije, Utrecht (NL); Carla Christina Schrier, Boxmeer (NL)

(73) Assignees: Utrech University, Utrecht (NL); Intervet Inc., Madison, NJ (US)

( * ) Notice: Subject to any disclaimer, the term of this patent is extended or adjusted under 35 U.S.C. 154(b) by 0 days.

(21) Appl. No.: 14/001,719

(22) PCT Filed: Mar. 1, 2012

(86) PCT No.: PCT/EP2012/053493
§ 371 (c)(1),
(2), (4) Date: Aug. 27, 2013

(87) PCT Pub. No.: WO2012/117045
PCT Pub. Date: Sep. 7, 2012

(65) Prior Publication Data
US 2014/0127264 A1    May 8, 2014

(30) Foreign Application Priority Data
Mar. 2, 2011    (EP) ..................... 11156526

(51) Int. Cl.
*A61K 39/215*    (2006.01)
*C07K 14/005*    (2006.01)
*A61K 39/12*    (2006.01)
*A61K 39/00*    (2006.01)

(52) U.S. Cl.
CPC ............ *A61K 39/215* (2013.01); *A61K 39/12* (2013.01); *C07K 14/005* (2013.01); *A61K 2039/525* (2013.01); *A61K 2039/5256* (2013.01); *A61K 2039/552* (2013.01); *C07K 2319/735* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| 6,296,852 | B1 | 10/2001 | Johnson et al. |
| 2005/0106177 | A1 | 5/2005 | Sodroski et al. |

FOREIGN PATENT DOCUMENTS

| EP | 0431668 B1 | 11/1990 |
| EP | 1241177 A1 | 9/2002 |
| WO | 02/092827 A2 | 11/2002 |
| WO | 2005/063801 A2 | 7/2005 |
| WO | 2007/030803 A2 | 3/2007 |
| WO | 2007106882 A2 | 9/2007 |
| WO | 2010/032235 A1 | 1/2010 |
| WO | 2010/148434 A1 | 12/2010 |
| WO | 2011/008974 A2 | 1/2011 |

OTHER PUBLICATIONS

Worthington et al., Avian Pathol. Jun. 2008; vol. 37(3): pp. 247-257.*
Johnson et al. 2003 Vaccine vol. 21, pp. 2730-2736.*
Casais et al., "Recombinant Avian Infectious Bronchitis Virus Expressing a Heterologous Spike Gene Demonstrates that the Spike Protein is a Determinant of Cell Tropism", Journal of Virology, 2003, pp. 9084-9089, vol. 77(16).
Cavanagh, Dave, "Severe acute respiratory syndrome vaccine development: experiences of vaccination against avian infectious bronchitis coronavirus", Avian Pathology, 2003, pp. 567-582, vol. 32(6).
Cavanagh, Dave, "Coronavirus avian infectious bronchitis virus", Vet. Res., 2007, pp. 281-297.
De Groot et al., "Evidence for a Coiled-coil Structure in the Spike Proteins of Coronaviruses", J. Mol. Biol., 1987, pp. 963-966, vol. 196.
Johnson et al., "A recombinant fowl adenovirus expressing the SI gene of infectious bronchitis virus protects against challenge with infectious bronchitis virus", Vaccine, 2003, pp. 2730-2736, vol. 21.
Kam et al., "Antibodies against trimeric S glycoprotein protect hamsters against SARS-CoV challenge despite their capacity to mediate FcγRII-dependent entry into B cells in vitro", Vaccine, 2007, pp. 729-740, vol. 25.
Kingham et al., "Identification of Avian Infectious Bronchitis Virus by Direct Automated Cycle Sequencing of the S-1 Gene", Avian Diseases, 2000, pp. 325-335, vol. 44.
Kuo et al., "Retargeting of Coronavirus by Substitution of the Spike Glycoprotein Ectodomain: Crossing the Host Cell Species Barrier", Journal of Virology, 2000, pp. 1393-1406, vol. 74(3).
Lenstra et al., "Antigenicity of the Peplomer Protein of Infectious Bronchitis Virus", Molecular Immunology, 1989, pp. 7-15, vol. 26(1).
Song et al., "Induction of protective immunity in chickens vaccinated with infectious bronchitis virus S1 glycoprotein expressed by a recombinant baculovirus", Journal of General Virology, 1998, pp. 719-723, vol. 79.

(Continued)

*Primary Examiner* — Shanon A Foley
*Assistant Examiner* — Myron Hill

(57) ABSTRACT

The present invention relates to Infectious bronchitis virus (IBV) spike protein or a fragment thereof comprising a receptor-binding domain, wherein said spike protein or said fragment thereof is C-terminally fused to a trimerisation or tetramerisation domain. Such proteins form trimer or tetramer structures and as such they mimic the natural context of the spike protein. The present invention further relates to subunit vaccines comprising such a protein, to DNA molecules encoding such proteins, to plasmids comprising such DNA molecules, to avian live recombinant carrier viruses (LRCV's) comprising such DNA molecules or plasmids, to vaccines comprising such DNA molecules, plasmids and LRCV's and to combination vaccines comprising an IBV spike protein, DNA molecules, plasmids or LRCV's encoding such a protein, and another IBV vaccine capable of inducing protection against another IBV serotype and/or a vaccine capable of inducing protection against another avian pathogen.

20 Claims, 6 Drawing Sheets

(56) References Cited

OTHER PUBLICATIONS

Figure 1:
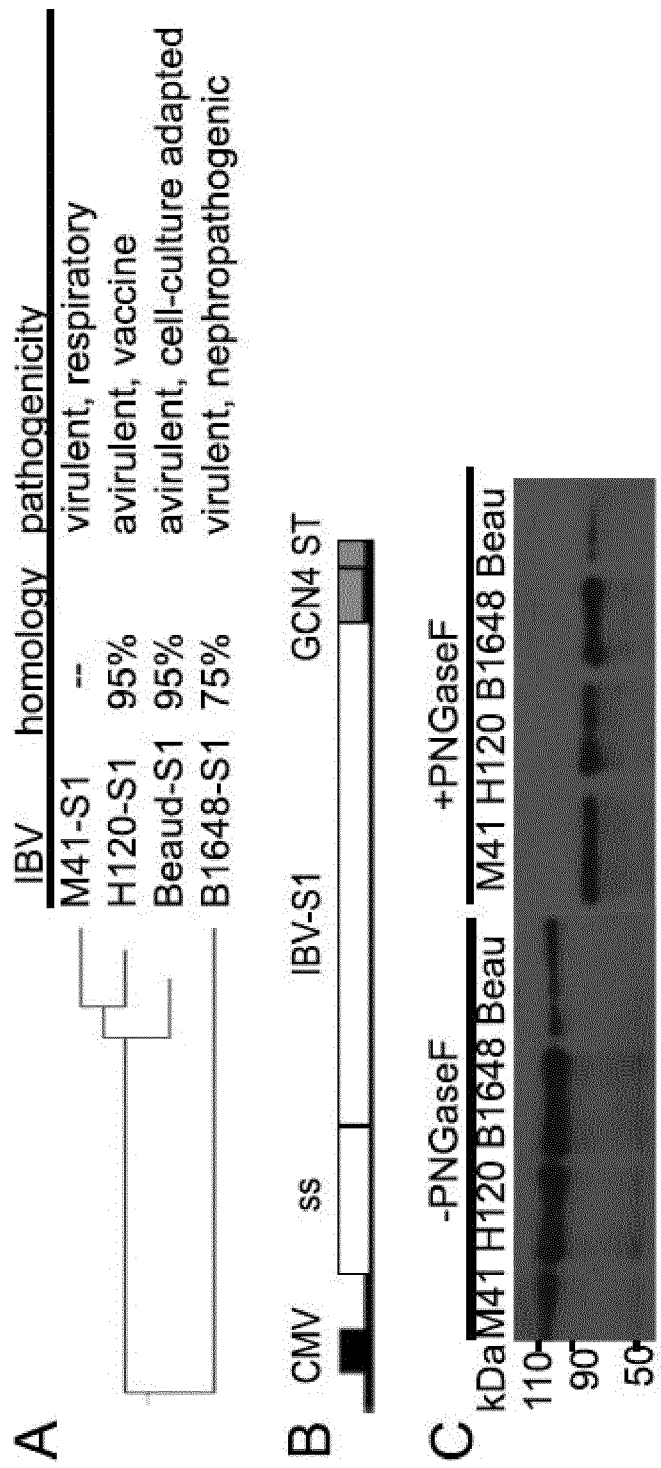

Wang et al., "Characterisation and evaluation of antiviral recombinant peptides based on the heptad repeat regions of NDV and IBV fusion glycoproteins", Virology, 2011, pp. 65-74, vol. 146.

Weiss et al., "Coronavirus Pathogenesis and the Emerging Pathogen Severe Acute Respiratory Syndrome Coronavirus", Microbiology and Molecular Biology Reviews, 2005, pp. 635-664, vol. 69(4).

Weissenhorn et al., "Assembly of a rod-shaped chimera of a trimeric GCN4 zipper and the HIV-1 gp41 ectodomain expressed in *Escherichia coli*", Proceedings of the National Academy of Sciences USA, 1997, pp. 6065-6069, vol. 94.

Wickramasinghe et al., "Binding of Avian Coronavirus Spike Proteins to Host Factors Reflects Virus Tropism and Pathogenicity", Journal of Virology, 2011, pp. 8903-8912, vol. 85(17).

Yang et al., "Highly Stable Trimers Formed by Human Immunodeficiency Virus Type 1 Envelope Glycoproteins Fused with the Trimeric Motif of T4 Bacteriophage Fibritin", Journal of Virology, 2002, pp. 4634-4642, vol. 76(9).

Yip et al., "Investigation of Antibodfy-Dependent Enhancement (ADE) of SARS coronavirus infection and its role in pathogenesis of SARs", BMC Proceedings, 2011, p. 80, vol. 5 (Suppl. 1).

Zeng et al., "Characterization of humoral responses in mice immunized with plasmid DNAs encoding SARS-CoV spike gene fragments", Biochemical and Biophysical Research Communications, 2004, pp. 1134-1139, vol. 315.

International Search Report for corresponding PCT/EP2012/053493, mailed May 30, 2012.

Bosch, et al.,, The Coronavirus Spike Protein Is a Class I Virus Fusion Protein: Structural and Functional Characterization of the Fusion Core Complex, Journal of Virology, 200, pp. 88, vol. 77, No. 16.

Sondermeijer, Avian herpesvirus as a live viral vector for the expression of heterologous antigens, Vaccine, 1993, pp. 349-358, vol. 11 No. 3.

Swayne, D.E., et al, Recombinant paramyxovirus Type 1-avian Influenza H7 Virus as a Vaccine for Protection of Chickens against Influenza and Newcastle Disease, Avian Diseases, 2003, pp. 1047-1050, vol. 47.

Winter C., et al., Infection of the tracheal epithelium by infectious bronchitis virus is sialic acid dependent, Microbes and Infection, Apr. 1, 2008, pp. 367-373, vol. 10 No. 4.

\* cited by examiner

Spike histochemistry using recombinantly expressed spike proteins of IBV-M41 on chicken respiratory tract tissue

Figure 5

SEQUENCE LISTING

<160> NUMBER OF SEQ ID NOS: 7

<210> SEQ ID NO 1
<211> LENGTH: 4776
<212> TYPE: DNA
<213> ORGANISM: infectious bronchitis virus

<400> SEQUENCE: 1

```
ggaggccgat taaagggatt ttagacagga acggtacgcc agctggaccg cggtctttcg      60
gacttttgaa agtgatggtg gtggggaag gattcgaacc ttcgaagtcg atgacggcag     120
atttagagtc tgctcccttt ggccgctcgg gaacccacc acaggtaatg cttttactgg     180
cctgctccct tatcgggaag cggggcgcat catatcaaat gacgcgccgc tgtaaagtgt     240
tacgttgaga aagctgctcc ctgcttgtgt gttggaggtc gctgagtagt gcgcgagcaa     300
aatttaagct acaacaaggc aaggcttgac cgacaattgc atgaagaatc tgcttagggt     360
taggcgtttt gcgctgcttc gcgatgtacg ggccagatat acgcgttgac attgattatt     420
gactagttat taatagtaat caattacggg gtcattagtt catagcccat atatggagtt     480
ccgcgttaca taacttacgg taaatggccc gcctggctga ccgcccaacg accccgcc     540
```

```
attgacgtca ataatgacgt atgttcccat agtaacgcca atagggactt tccattgacg    600
tcaatgggtg gagtatttac ggtaaactgc ccacttggca gtacatcaag tgtatcatat    660
gccaagtacg cccectattg acgtcaatga cggtaaatgg cccgcctggc attatgccca    720
gtacatgacc ttatgggact ttcctacttg gcagtacatc tacgtattag tcatcgctat    780
taccatggtg atgcggtttt ggcagtacat caatgggcgt ggatagcggt ttgactcacg    840
gggatttcca agtctccacc ccattgacgt caatgggagt ttgttttggc accaaaatca    900
acgggacttt ccaaaatgtc gtaacaactc cgccccattg acgcaaatgg gcggaattcc    960
tgggcgggac tggggagtgg cgagccctca gatcctgcat ataagcagct gcttttgcc    1020 tgtactgggt ctctctggtt agaccagatc tgagcctggg agctctctgg ctaactagag   1080
aacccactgc ttaagcctca ataaagcttc tagagatccc tcgacctcga gatccattgt   1140
gctctaaagg agatacccgg ccagacaccc tcacctgcgg tgcccagctg cccaggctga   1200
ggcaagagaa ggccagaaac catgcccatg gggtctctgc aaccgctggc caccttgtac   1260
ctgctgggga tgctggtcgc ttccgtgcta gcagccctgt acgacagctc cagctatgtg   1320
tactattacc agagcgcctt tcgcccacca aacggatggc acctgcatgg aggagcttac   1380
gctgtggtga atatctccag cgagtccaac aatgctggct ccagcccagg atgcatcgtg   1440
ggcacaattc acgaggaag ggtggtgaac gcctccagca ttgctatgac cgctccatcc    1500
agcggaatgg cttggtccag ctcccagttc tgcacagccc actgtaattt tagcgacacc   1560
acagtgttcg tgacacattg ctataagtac gatggatgtc ccatcaccgg catgctgcag   1620
aagaactttc tgcgggtgtc cgccatgaag aacggccagc tgttctacaa tctgacagtg   1680
tccgtggcca gtatccaac ctttaagagc ttccagtgcg tgaacaatct gacctccgtg    1740
tacctgaacg gcgacctggt gtatacatcc aatgagacca cagatgtgac cagcgccgga   1800
gtgtacttta aggccggcgg acctatcacc tataaagtga tgagggaggt gaaggccctg   1860
gcctacttcg tgaatggcac agcccaggac gtgattctgt gcgatggaag ccctagggga   1920
ctgctggcct gtcagtacaa caccggaaat ttctccgatg gcttttatcc gttcatcaac   1980
agctccctgg tgaagcagaa gtttattgtg taccgcgaga cagcgtgaa taccacattc    2040 accctgcaca acttcacatt tcataatgag accggagcca ccccaatcc atccggcgtg    2100 cagaacatcc agacctacca gacccagaca gcccagtccg gctattacaa cttcaatttt   2160
agcttcctga gctcctttgt gtataaggag agcaacttca gtacggctc ctatcacccc    2220 agctgcaatt ttcggctgga gaccatcaac aatggactgt ggttcaacag cctgtccgtg   2280
agcattgcct acggccctct gcagggcggc tgtaagcagt ccgtgtttag cggaagggcc   2340
acctgctgtt atgcctactc ctatggcgga ccgagcctgt gcaagggagt gtactccggc   2400
gagctggacc tgaatttcga gtgtggcctg ctggtgtatg tgaccaagtc cggaggaagc   2460
cgcatccaga ccgctacaga gcctcccgtg atcaccaggc ataactacaa caatattacc   2520
ctgaacacat gcgtggatta caatatctat ggcaggaccg gccagggatt cattaccaac   2580
gtgacagact ccgccgtgag ctacaattat ctggccgatg ctggactggc catcctggac   2640
acctccggca gcatcgatat ttttgtggtg cagggcgagt acggactgac atattacaag   2700
gtgaacccct gtgaggacgt gaatcagcag ttcgtggtga gcggcggaaa gctggtggga   2760
attctgacat ccaggaacga gaccggcagc cagctgctgg agaaccagtt ctacatcaag   2820
attaccaatg gcacaggcgg aggggtaccg gatccattaa ttaagcgcat gaagcagatc   2880
```

-continued

| | |
|---|---|
| gaggacaaga tcgaagagat cgagtccaag cagaagaaga tcgagaacga gatcgcccgc | 2940 |
| atcaagaaga ttaagctggt gccgcgcggc agcctcgagt ggagccaccc gcagttcgag | 3000 |
| aagtgaattc tgcagatatc cagcacagtg gcggccgcga ctctagagga tctttgtgaa | 3060 |
| ggaaccttac ttctgtggtg tgacataatt ggacaaacta cctacagaga tttaaaaaac | 3120 |
| ctcccacacc tccccctgaa cctgaaacat aaaatgaatg caattgttgt tgttaacttg | 3180 |
| tttattgcag cttataatgg ttacaaataa agcaatagca tcacaaattt cacaaataaa | 3240 |
| gcatttttt cactgcattc tagttgtggt ttgtccaaac tcatcaatgt atcttatcat | 3300 |
| gtctggggaa gatcgatctt ccgatcctgt ggaatgtgtg tcagttaggg tgtggaaagt | 3360 |
| cccccaggctc cccagcaggc agaagtatgc aaagcatgca tctcaattag tcagcaacca | 3420 |
| ggtgtggaaa gtccccaggc tccccagcag gcagaagtat gcaaagcatg catctcaatt | 3480 |
| agtcagcaac catagtcccg cccctaactc cgcccatccc gcccctaact ccgcccagtt | 3540 |
| ccgcccattc tccgcccat ggctgactaa ttttttttat ttatgcagag gccgaggccg | 3600 |
| cctcggcctc tgagctattc cagaagtagt gaggaggctt ttttggaggc ctaggctttt | 3660 |
| gcaaaaagct aattcggcgt aatctgctgc ttgcaaacaa aaaaaccacc gctaccagcg | 3720 |
| gtggtttgtt tgccggatca agagctacca actctttttc cgaaggtaac tggcttcagc | 3780 |
| agagcgcaga taccaaatac tgtccttcta gtgtagccgt agttaggcca ccacttcaag | 3840 |
| aactctgtag caccgcctac atacctcgct ctgctgaagc cagttaccag tggctgctgc | 3900 |
| cagtggcgat aagtcgtgtc ttaccgggtt ggactcaaga atagttacc ggataaggcg | 3960 |
| cagcggtcgg gctgaacggg gggttcgtgc acacagccca gcttggagcg aacgacctac | 4020 |
| accgaactga gatacctaca gcgtgagcta tgagaaagcg ccacgcttcc cgaagggaga | 4080 |
| aaggcggaca ggtatccggt aagcggcagg gtcggaacag gagagcgcac gagggagctt | 4140 |
| ccagggggaa acgcctggta tctttatagt cctgtcgggt ttcgccacct ctgacttgag | 4200 |
| cgtcgatttt tgtgatgctc gtcagggggg cggagcctat ggaaaaacgc cagcaacgca | 4260 |
| agctagattt tgttaaaatt cgcgttaaat ttttgttaaa tcagctcatt ttttaaccaa | 4320 |
| taggccgaaa tcggcaaaat cccttataaa tcaaaagaat agcccgagat agggttgagt | 4380 |
| gttgttccag tttggaacaa gagtccacta ttaaagaacg tggactccaa cgtcaaaggg | 4440 |
| cgaaaaaccg tctatcaggg cgatggccgc ccactacgtg aaccatcacc caaatcaagt | 4500 |
| tttttggggt cgaggtgccg taaagcacta atcggaacc ctaaagggag cccccgattt | 4560 |
| agagcttgac ggggaaagcc ggcgaacgtg gcgagaaagg aagggaagaa agcgaaagga | 4620 |
| gcgggcgcta gggcgctggc aagtgtagcg gtcacgctgc gcgtaaccac cacacccgcc | 4680 |
| gcgcttaatg cgccgctaca gggcgcgtac tatggttgct ttgacgagca cgtataacgt | 4740 |
| gctttcctcg ttagaatcag agcgggagct aaacac | 4776 |

<210> SEQ ID NO 2
<211> LENGTH: 32
<212> TYPE: PRT
<213> ORGANISM: artificial sequence
<220> FEATURE:
<223> OTHER INFORMATION: polymerisation domain

<400> SEQUENCE: 2

Arg Met Lys Gln Ile Glu Asp Lys Ile Glu Ile Leu Ser Lys Gln Tyr
1               5                   10                  15

His Ile Glu Asn Glu Ile Ala Arg Ile Lys Lys Leu Ile Gly Glu Arg
            20                  25                  30

<210> SEQ ID NO 3
<211> LENGTH: 36
<212> TYPE: PRT
<213> ORGANISM: artificial sequence
<220> FEATURE:
<223> OTHER INFORMATION: polymerisation domain

<400> SEQUENCE: 3

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Val Pro Arg
            20                  25                  30

Gly Ser Leu Glu
35

<210> SEQ ID NO 4
<211> LENGTH: 27
<212> TYPE: PRT
<213> ORGANISM: artificial sequence
<220> FEATURE:
<223> OTHER INFORMATION: polymeriasation domain

<400> SEQUENCE: 4

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 5
<211> LENGTH: 36
<212> TYPE: PRT
<213> ORGANISM: artificial sequence
<220> FEATURE:
<223> OTHER INFORMATION: polymerisation domain

<400> SEQUENCE: 5

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Val Pro Arg
            20                  25                  30

Gly Ser Leu Glu
35

<210> SEQ ID NO 6
<211> LENGTH: 32
<212> TYPE: PRT
<213> ORGANISM: Artificial sequence
<220> FEATURE:
<223> OTHER INFORMATION: polymerisation domain

<400> SEQUENCE: 6

Met Lys Gln Ile Glu Asp Lys Leu Glu Glu Ile Leu Ser Lys Leu Tyr
1               5                   10                  15

His Ile Glu Asn Glu Ile Ala Arg Ile Lys Lys Leu Leu Gly Glu Arg
            20                  25                  30

<210> SEQ ID NO 7
<211> LENGTH: 8
<212> TYPE: PRT
<213> ORGANISM: artificial sequence
<220> FEATURE:
<223> OTHER INFORMATION: Strep tag

```
<400> SEQUENCE: 7

Trp Ser His Pro Gln Phe Glu Lys
1               5
```

INFECTIOUS BRONCHITIS VIRUS (IBV) SPIKE PROTEIN AS SUBUNIT VACCINE

CROSS-REFERENCE TO RELATED APPLICATIONS

This application is a national stage entry under 35 U.S.C. §371 of PCT/EP2012/053493, filed on Mar. 1, 2012, which claims priority to U.S. Provisional Application No. 61/448,464, filed on Mar. 2, 2011, and EP Application No. 11156526.3, filed on Mar. 5, 2010. The content of PCT/EP2012/053493 is hereby incorporated by reference in its entirety.

The present invention relates to IBV spike proteins, to subunit vaccines comprising such a protein, to DNA molecules encoding such proteins, to plasmids comprising such DNA molecules, to avian live recombinant carrier viruses (LRCV's) comprising such DNA molecules or plasmids, to vaccines comprising such DNA molecules, plasmids and LRCV's and to combination vaccines comprising an IBV spike protein, DNA molecule, plasmid or LRCV's encoding such a protein, and another IBV vaccine capable of inducing protection against another IBV serotype and/or a vaccine capable of inducing protection against another avian pathogen.

Infectious bronchitis (IB) is an acute, highly contagious respiratory disease of domestic fowl (chicken), caused by Infectious Bronchitis virus (IBV). Clinical signs of IB include sneezing/snicking, tracheal rales, nasal discharge and wheezing. Clinical signs are more obvious in chicks than in adult birds. The birds may appear depressed and consume less food. Meat-type birds have reduced weight-gain, whilst egg-laying birds lay fewer eggs. The respiratory infection predisposes chickens to secondary bacterial infections, which can be fatal in chicks. The virus can also cause permanent damage to the oviduct, especially in chicks, leading to reduced egg production and quality, and kidney, sometimes leading to kidney disease, which can be fatal.

Infectious Bronchitis virus (IBV) is a member of the genus Coronavirus, family Coronaviridae. It has a positive sense, single-stranded RNA genome of approximately 28 000 nucleotides associated with a nucleocapsid protein, N, surrounded by a lipid membrane/envelope. Three other viral proteins are associated with the envelope: the large spike glycoprotein, S; a smaller integral membrane protein, M; and the E protein, the smallest of the envelope-associated proteins.

The coronavirus Spike (S) protein is a type I glycoprotein observable by electron microscopy as coronavirus virion spikes. The S protein is assembled into virion membranes, possibly through non-covalent interactions with the M protein, but is not required for formation of coronavirus virus-like particles. Following incorporation into coronavirus particles, determined by the carboxy-terminal domain, the S glycoprotein is responsible for binding to the target cell receptor and fusion of the viral and cellular membranes, fulfilling a major role in the infection of susceptible cells. Furthermore, the IBV spike protein is involved in the induction of a protective immune response when inoculated into chickens (for a review see Cavanagh, D., Vet. Res. 38: 281-297 (2007)).

All coronavirus S glycoproteins consist of four domains; a signal sequence, that is cleaved off during synthesis, the ectodomain which is present on the outside of the virion particle, the transmembrane region responsible for anchoring the S protein into the lipid bi-layer of the virion particle, and the cytoplasmic tail that might interact with other IBV proteins, such as the membrane protein (E) and integral membrane protein (M). The IBV S glycoprotein (about 1162 amino acids) is cleaved into two subunits, S1 (about 535 amino acids and about 90-kDa) and S2 (about 627 amino acids and about 84-kDa). The C-terminal S2 subunit associates non-covalently with the N-terminal S1 subunit and contains the transmembrane and C-terminal cytoplasmic tail domains. The S1 subunit contains the receptor-binding activity of the S protein.

In previous studies with other corona viruses, murine hepatitis virus (MHV) and transmissible gastroenteritis virus (TGEV), a spike gene of a (virulent) donor virus strain was used to replace the spike gene of a receiver virus strain to investigate the determinants of pathogenesis and cell tropism. These studies showed that both the in vitro properties (cell tropism) and in vivo properties (virulence) of the donor virus strain were acquired by the receiver virus strain. It was concluded that the spike gene is a determinant of cell tropism and virulence (Phillips et al., J. Virol. 73, 7752-7760, 1999; Sanchez et al., J. Virol. 73, 7607-7618, 1999; Das Sarma et al., J. Virol. 74, 9206-9213, 2000; Navas et al., J. Virol. 75, 2452-2457, 2001 and Kuo et al., J. Virol. 74, 1393-1406, 2000; international patent application WO 01/39797). International patent application WO 98/49195 discloses a coronavirus (e.g. MHV) in which a part of the spike protein gene has been replaced by the corresponding part of the spike protein gene of an unrelated coronavirus (e.g. FIPV), thereby acquiring another cell substrate specificity allowing the recombinant virus to target other cell types. For IBV, replacement experiments have been done, where the ectodomain of the spike protein of the Baudette strain was replaced by that of the spike protein of the pathogenic M41 strain. (Casais, R. et al., J. Virol. 77: 9084-9089 (2003), Hodgson, T. et al., J. Virol. 78: 13804-13811 (2004). In these experiments it was confirmed that the spike protein is indeed a determinant of cell tropism.

IBV exhibits great antigenic variation, initially recognized as different serotypes. Serotypic strain classification of IBV strains is based on the ability of one strain to induce virus neutralizing antibodies effective against another strain (Cook et al., Avian Pathol. 13, 733-741, 1984). The most variable protein of IBV is the spike protein. It defines the serotype and is the major inducer of protective immune responses. An IBV vaccine virus of one serotype induces immune responses that often protect poorly against IBV of other serotypes, because of the differences in the S proteins. Consequently IB vaccines have been developed against many serotypes. However, previously unknown serotypes are continually emerging, creating a requirement for new, homologous vaccine viruses.

Both live and inactivated virus vaccines are used in IB vaccination. To date, the most efficacious vaccines are live attenuated viruses empirically produced following blind repeated passages through embryonated eggs until a desired balanced degree of attenuation and immunogenicity has been achieved. Such vaccines are genetically ill-defined and the molecular basis of the attenuation is unknown. Disadvantageously, upon serial passaging the immunogenicity of the virus decreases which often results in safe but less efficacious vaccine viruses. Producing IBV vaccine strains having a 'balanced' degree of attenuation; moderate to low pathogenicity but still able to induce a strong immune responses—is a trial and error approach that renders the outcome of this conventional attenuation approach uncertain.

For this reason, inactivated vaccines would seem the vaccines of choice in the battle against IBV infection. To this end, as early as 1960 the first inactivated oil-emulsion IBV whole virus vaccines were made.

It was however found that, although some protection was obtained, the overall effect of such vaccines was disappointing.

Such vaccines do not provide protection against deciliation of the ciliated epithelia of the respiratory tract (Box, P. G. et al., Vet. Rec. 106: 264-268 (1980), Martins, N. R et al., Avian Dis. 35: 470-475 (1991), McDougall, J. S. et al., Vet. Rec. 85: 378-381 (1969), Muneer, M. A. et al., Avian Dis. 31: 820-828 (1987)).

More recent studies therefore concentrated on the use of purified inactivated IBV as a vaccine, but again these vaccines were not very successful, giving respiratory tract protection below 60% (Cavanagh, D. et al., J. Gen. Virol. 67: 1435-1442 (1986), Cavanagh, D. et al., Avian Pathol. 32: 567-582 (2003), Ignjatovic, J. et al., Arch. Virol. 138: 117-134 (1994), Song, C. S. et al., J. Gen. Virol. 79: 719-723 (1998)).

The S1 subunit of the spike protein has also been used for vaccination purposes. S1 protein prepared from purified viruses, as well as baculo-expressed S1 have been tested as vaccines. But again, the protective properties of such vaccines turned out to be disappointing. Even after multiple vaccinations, the protection level remained below 50% protection. (Song, C. S. et al., J. Gen. Virol. 79: 719-723 (1998), Cavanagh, D. et al., J. Gen. Virol. 67: 1435-1442 (1986), Ignjatovic, J. et al., Arch. Virol. 138: 117-134 (1994)).

It is known that other proteins, such as e.g. the replicase gene of IBV can play a role in the pathogenic nature of coronaviruses (Navas, S. et al., J. Virol. 77: 4972-4978 (2003), Weiss, S. R., Microbiol. Mol. Biol. Rev. 69: 635-664 (2005), Armesto, M. et al., Plos One vol. 4, issue 10, October 2009: e7384).

Thus, on the basis of the failure of spike protein based vaccines to induce a high level of protection, and in view of the fact that indeed other proteins can play a role in pathogenesis of IBV, it may be assumed that subunit vaccines solely on the basis of spike protein are simply not capable of inducing a high level of protection. Anyway, for the reasons given above, highly effective vaccines on the basis of spike protein would not seem feasible. It is thus clear that there exists a need for new IBV vaccines that combine the safety of inactivated IBV vaccines with a higher level of protection against IBV infection.

It is an objective of the present invention to provide such vaccines.

It was now surprisingly found, that if a so-called trimerisation or tetramerisation domain (vide infra) is fused to the C-terminus of a spike protein, or at least to a fragment of the spike protein that is responsible for the recognition of the host cell (the receptor-binding domain), these spikes or such fragments thereof, carrying the trimerisation or tetramerisation domain were capable of forming trimeric or tetrameric spike structures (spike dimers or spike trimers), possibly present in multimeric complexes, that were capable of attaching to susceptible chicken cells.

This indicates that such trimeric or tetrameric spike structures mimic the natural conformation of the spike protein as present on the virus.

And that in turn means that, contrary to monomeric or even dimeric spike structures, due to their natural conformation these trimeric or tetrameric spike structures are able to induce an immune response against the natural conformation of the spike protein.

The difference in binding capabilities of spikes expressed as dimers and trimers is shown in FIG. 5. This figure convincingly shows that spike proteins carrying a dimerisation domain (as is also the case for monomeric spike proteins) are not capable of binding to trachea or lung cells, whereas in sharp contrast trimeric structures of spike proteins carrying a trimerisation domain bind strongly to both tracheal cells and lung cells.

Thus, a first embodiment of the invention relates to an Infectious Bronchitis virus (IBV) spike protein or an immunogenic fragment thereof comprising the receptor-binding domain, characterised in that said spike protein or immunogenic fragment thereof comprising the receptor-binding domain is C-terminally fused to a trimerisation or tetramerisation domain.

In general, the signal sequence, the ectodomain, the transmembrane region and the cytoplasmic tail domain of IBV spike proteins cover the amino acid fragments 1-18, 19-1091, 1092-1119 and 1120-1162, respectively (numbers refer to Beaudette-CK, Casais et al., J. Virol. 75, 12359-12369, 2001; S proteins from other strains of IBV may differ in the number of amino acids due to small deletions and/or insertions). In addition, also the amino acid sequence at the S1/S2 cleavage site of IBV is well known. For Beaudette the S1 and S2 polypeptides span amino acid 1 (19)-535 and 536-1162, respectively.

In principle, the trimerisation or tetramerisation domain can be fused to the C-terminal amino acid of the whole spike protein. It is however also possible to use a shorter fragment of the spike protein, with the proviso that the receptor-binding domain of the spike (the fragment binding to the chicken cells) remains present. The receptor-binding domain is located in the S1 polypeptide. More specifically, it is known to be located at the N-terminus of the S1 polypeptide, since it has been shown that this region is responsible for binding to tracheal cells. So basically, not the whole S1 polypeptide needs to be present, provided that the receptor-binding domain is present. Preferably, a stretch of amino acids adjacent to the signal sequence and at least comprising the receptor-binding domain is present. For the Baudette strain this would e.g. be at least the region from amino acid 19-232 of the S1 polypeptide. Since the fragment must be immunogenic, the fragment should also comprise immunogenic sites. These immunogenic sites have been mapped for IBV and several of these sites are located in the region between 19 and 149, which is well within the region from amino acid 19-232 of the S1 polypeptide. However, since other immunogenic sites are located between position 291 and 398, the immunogenic fragment should preferably comprise at least the region from amino acid 19 to 398. More preferably, the fragment comprises at least the whole S1 polypeptide. (Kant, A. et al., J. General Virol. 73: 591-596 (1992).

A trimerisation or tetramerisation domain is understood to be a stretch of amino acids that is capable of forming a three-stranded or four-stranded coiled coil. Coiled coil proteins form a group of proteins composed of interacting amphipathic α helices. Coiled coil proteins have a characteristic seven residue repeat (a b c d e f g)$_n$ having hydrophobic residues at positions a and d, and polar residues generally elsewhere. Although coiled coil proteins all share this pattern of hydrophobic and polar residues, they are found, depending on the exact amino acids, to exist in dimeric, trimeric and tetrameric conformations. Examples of such two-, three- and four-stranded coiled coil proteins are given in O'Shea, E. K. et al., Science 254: 539-254 (1991), Harbury, P. B. et al., Science 262: 1401-1407 (1993), Eckert, D. M. et al., J. Mol. Biol. 284: 859-865 (1998). The coiled coil proteins mentioned in these publications are referred to as GCN4-domains.

Thus, a trimerisation or tetramerisation domain as used in the invention is a stretch of amino acids that is capable of forming a three-stranded or four-stranded coiled coil.

An example of an amino acid sequence of such a domain is the sequence of the GCN4-pI$_O$I domain: Ac-RMKQIED-KIEILSKQYHIENEIARIKKLIGER (SEQ ID NO: 2). Another example of a GCN4-sequence is the amino acid sequence used in the Example section (vide infra): RMKQ-IEDKIEEIESKQKKIENEIARIKKLVPRGSLE (SEQ ID NO: 3).

Another example of a trimerisation domain is the trimerisation domain of T4 bacteriophage fibritin (Xinzhen Yang et al., J. Virol. 76: 4634-4642 (2002)). An example of the amino acid sequence of a fibritin trimerisation domain is GYIPEAPRDGQAYVRKDGEWVLLSTFL (SEQ ID NO: 4).

Preferably, the trimerisation domain with the GCN4-sequence RMKQIEDKIEEIESKQKKIENEIARIK-KLVPRGSLE (SEQ ID NO: 5) is used in the invention.

An example of a tetramerisation domain is the yeast GCN4 leucine zipper mutant that forms a tertramer: MKQ-IEDKLEEILSKLYHIENEIARIKKLLGER (SEQ ID NO: 6) (Leclerc D. et al., J. Biol Chem. 273: 29015-29021 (1998).

A trimeric or tetrameric spike protein structure is understood to be a complex of three or four spike proteins or immunogenic fragments thereof comprising the receptor-binding domain that are kept together by the trimerisation or tetramerisation domain fused to the C-terminal end of each of the spike proteins. They thus form a trimeric or tetrameric structure. It should be kept in mind that the wording "trimeric or tetrameric spike structure" (or briefly; a trimer or tetramer) in this invention should be understood as existing of three or four whole spike proteins but equally of three or four immunogenic fragments of spike proteins, each comprising the receptor-binding domain.

The formation of trimeric or tetrameric spike structures occurs spontaneously in the cell. Monomeric spikes on the one hand, and trimeric or tetrameric spike structures on the other hand can easily be distinguished on non-denaturing gels and by means of gel filtration column chromatography. On non-denaturing gels, trimeric or tetrameric spike structures show a band that runs much higher than that of monomeric spikes. Trimeric or tetrameric spike structures can be reduced to monomeric spikes after boiling, in which case they co-migrate with the monomeric form. In a gel filtration column chromatography elution pattern, trimeric and tetrameric spikes peak as complexes of double or triple trimers or of double or triple tetramers.

Therefore, another embodiment of the present invention relates to trimeric or tetrameric spike protein structures of infectious bronchitis virus (IBV) spike protein or an immunogenic fragment thereof comprising a receptor-binding domain, according to the invention.

Preferably, the spike protein or the immunogenic fragment thereof comprising the receptor-binding domain is derived from a (virulent) IBV from the field. Spike genes can be isolated from any available IBV strain irrespective of its serotype by standard techniques commonly used in the art for this purpose.

More preferably, the present invention concerns an IBV spike protein or a fragment thereof comprising the receptor-binding domain, according to the invention, wherein the spike is of an IBV Massachusetts serotype, in particular of IBV strain M41, or of an IBV 793B serotype, in particular of IBV strain 4/91.

Therefore, a most preferred form of this embodiment relates to a IBV spike protein or a fragment thereof comprising the receptor-binding domain, according to the invention, characterised in that said IBV spike protein is a spike protein of IBV strain M41.

Another similarly preferred form of this embodiment relates to a IBV spike protein or a fragment thereof comprising the receptor-binding domain, according to the invention, characterised in that said IBV spike protein is a spike protein of IBV strain 4/91.

The word "fused" is understood to mean that the N-terminal amino acid of a trimerisation or tetramerisation domain is covalently linked to the C-terminal amino acid of a spike protein or a fragment thereof that at least comprises the receptor-binding domain of that spike protein Such a fusion protein in which the N-terminal amino acid of a trimerisation or tetramerisation domain is covalently linked to the C-terminal amino acid of a spike protein can be obtained by cloning a DNA molecule encoding a trimerisation or tetramerisation domain downstream of a DNA molecule that encodes at least the receptor-binding domain of a spike protein. This can be done through standard cloning techniques, well-known in the art and as e.g. described in text books such as Molecular Cloning: A Laboratory Manual, Cold Spring Harbor Laboratory press, by Joseph Sambrook, Peter MacCallum Cancer Institute, Melbourne, Australia; David Russell, University of Texas Southwestern Medical Center, Dallas, ISBN 978-087969577-4 (2001).

The two DNA molecules must of course be ligated in such a manner that the reading frame of the trimerisation or tetramerisation domain is not disturbed. If necessary, a (preferably short) linker DNA, preferably with suitable restriction sites can be used to facilitate in-frame cloning of the two DNA molecules.

A specific process for obtaining a fusion protein according to the invention is described in the Examples section.

Figure 6:
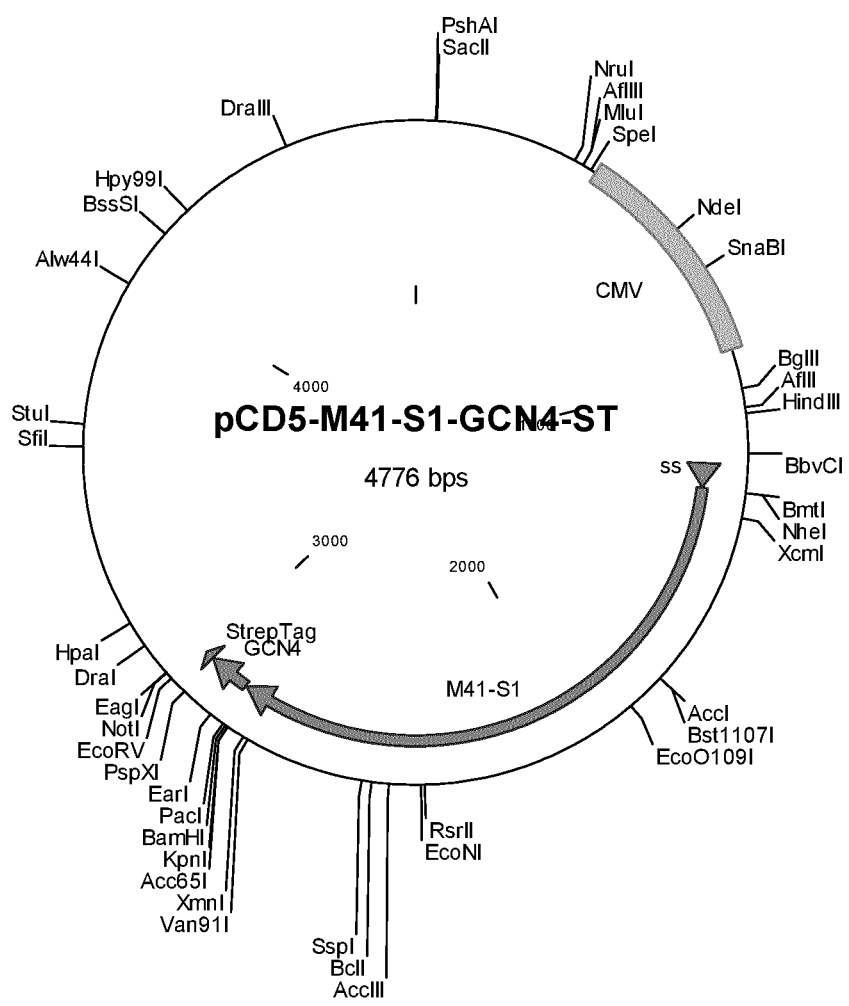

In addition, FIG. 1B gives an example of how the trimerisation or tetramerisation domain (the GCN4 domain) can be located in relation to the IBV-S1 region of the spike gene. FIG. 6 gives a detailed example of a plasmid marked pCD5-M41S1-GCN4-ST that comprises a GCN4 domain fused to the S1 subunit of the M41 spike.

SEQ ID NO.: 1 provides the full sequence of that plasmid. The location of the CMV promoter used here, corresponds to nucleotides 434-954 of SEQ ID NO.: 1, the pCD5-signal sequence corresponds to nucleotide 1222-1286, the M41-S1 subunit corresponds to nucleotide 1294-2835, the GCN4-domain corresponds to nucleotide 2866-2979 and the Strep-tag corresponds to nucleotide 2980-3003.

In the Examples, a heterologous (non-IBV, but human) CD5 signal sequence was used. The reason for this is, that expression has been done in mammalian cells, and the codon usage of the CD5 signal sequence is optimised for use in these mammalian cells. The use of a homologous IBV-signal sequence, preferably codon-optimised, would however also be very suitable.

Examples of typical IBV reference strains and the nucleotide sequence database accession numbers of their spike gene sequences are M41 (Massachusetts serotype; X04722), NL/D274/78 (D274 serotype; X15832), USA/Arkansas 99 (Ark 99 serotype; L10384), Belgium/B1648 (B1648 serotype; X87238), USA(DE)/072/92 (DE072 serotype; U77298), US(GA)/0470/98 (Georgia 98 serotype;

AF274437), UK/4/91 (793B1 serotype; AF093794), USA/Connecticut (Connecticut serotype; L18990) and NL/D1466 (D1466 serotype; M21971).

The cloning of various IBV spike genes is described in Adzhar et al., Avian Path. 26, 625-640, 1997; Shaw et al., Avian Pathol. 25, 607-611, 1996; Binns et al., J. Gen. Virol. 67, 2825-2831, 1986 and Binns et al., J. Gen Virol. 66, 719-726, 1985).

Thus, another embodiment of the present invention relates to a DNA molecule characterised in that said DNA molecule encodes an IBV spike protein or an immunogenic fragment thereof comprising the receptor-binding domain, that carries a C-terminally fused trimerisation or tetramerisation domain.

Expression of a DNA molecule encoding a fusion protein comprising at least the receptor-binding domain of an IBV spike protein and a trimerisation or tetramerisation domain can be obtained by cloning of this DNA molecule into a plasmid that comprises an upstream promoter capable of transcribing said downstream located DNA molecule. Thus, the DNA to be transcribed would be under the control of said promoter. Expression of the desired protein is subsequently obtained in a cell that recognises the promoter.

When the host cell is yeast, useful expression control sequences include, e.g., α-mating factor. Ready-to-use expression systems are i.a. commercially available from Research Corp. Technologies, 5210 East Williams Circle, Suite 240, Tucson, Ariz. 85711-4410 USA For insect cells the classical polyhedrin or p10 promoter of baculoviruses can be used (Smith, G. E. et al., Mol. Cell. Biol. 3, 2156-65, 1983). When the host cell is of vertebrate origin, useful expression control sequences include classic promoters such as the (human) cytomegalovirus immediate early promoter (Seed, B. et al., Nature 329, 840-842, 1987; Fynan, E. F. et al., PNAS 90, 11478-11482, 1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well known bovine growth hormone poly-adenylation sequence, the SV40 poly-adenylation sequence, the human cytomegalovirus (hCMV) terminator and poly-adenylation sequences.

Yeast, fungal, insect and vertebrate cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are attractive expression systems. Such systems are e.g. described in the French Patent Application with Publication number 2 714 074, and in US NTIS Publication No US 08/043,109 (Hoffman, S, and Rogers, W.: Public. Date 1 Dec. 1993).

Preferred cells or cell lines for expression of the spike protein according to the invention are e.g. mammalian cells like HEK293 and HEK293T cells, Hela cells, Chinese Hamster Ovary cells, or Madin-Darby canine kidney-cells, also with appropriate vectors or recombinant viruses. Other preferred cells or cell lines are avian cells such as CEF, HD-11 or DT-40 cells.

Further ample guidance with regard to eukaryotic expression is given i.a. in recent text books on expression such as: Production of Recombinant Proteins: Novel Microbial and Eukaryotic Expression Systems, Publisher: Wiley-VCH, ISBN: 3527310363 edition 2005, and Expression systems, edited by Michael Dyson and Yves Durocher, Scion Publishing Ltd, ISBN 9781904842439 edition 2007.

Thus, another embodiment of the present invention relates to a plasmid characterised in that said plasmid comprises a DNA molecule encoding an IBV spike protein or an immunogenic fragment thereof comprising the receptor-binding domain, that carries an C-terminally fused trimerisation or tetramerisation domain, under the control of a promoter.

Trimeric or tetrameric spike protein structures according to the invention are very suitable as a basis for subunit vaccines for the protection of poultry against IBV infection. Such vaccines would then comprise an IBV spike protein structure or an immunogenic fragment thereof comprising the receptor-binding domain, according to the present invention and a pharmaceutically acceptable carrier.

Thus, another embodiment of the present invention relates to subunit vaccines for the protection of poultry against IBV infection, characterised in that such vaccines comprise an immunogenic amount of IBV spike protein or an immunogenic fragment thereof comprising the receptor-binding domain, according to the invention and a pharmaceutically acceptable carrier.

An immunogenic amount of IBV spike protein or a fragment thereof comprising the receptor-binding domain, according to the invention, is the amount of that protein that induces an immune response in chickens or turkeys that decreases the pathological effects of the disease, when compared to the pathological effects after infection with a wild-type IBV in non-immunized birds.

A typical subunit vaccine according to the invention would usually comprise between 10 μg-1 mg of the trimeric or tetrameric spike protein according to the invention. Amounts of less than 10 μg of the trimeric or tetrameric spike protein according to the invention would usually require the presence of an adjuvant. Amounts that exceed 1 mg are, although suitable, economically less attractive.

As the skilled person realises, the final amount of trimeric or tetrameric spike protein in a vaccine would be determined i.a. by the presence or absence of an adjuvant and the characteristics of that adjuvant.

Vaccines according to the present invention also comprise a pharmaceutically acceptable carrier customarily used for such active components. Carriers can be, or may include, stabilizers, diluents, preservatives and buffers. Suitable stabilizers are for example SPGA, carbohydrates (such as dried milk, serum albumin or casein) or degradation products thereof. Suitable buffers are for example alkali metal phosphates. Suitable preservatives are thimerosal, merthiolate and gentamicin. Diluents include water, aqueous buffers (such as buffered saline), alcohols and polyols (such as glycerol).

There are many adjuvants known in the art that are suitable in combination with the IBV spike protein or a fragment thereof comprising the receptor-binding domain, according to the invention, such as alum hydroxide, alumin phosphate, saponins, vegetable oils such as tocopherol and mineral oils. Very efficient adjuvants are oil-in-water emulsions and especially water-in-oil emulsions. Such emulsions are well-known in the art. Oil-in-water or water-in-oil emulsions can e.g. be based on a mineral oil, such as Bayol F® or Marcol 52® or a vegetable oil such as vitamin E acetate.

Preferably, a subunit vaccine according to the invention comprises an adjuvant.

The route of administration of the subunit vaccine is in principle the parenteral route. Administration can be done e.g. intramuscular or subcutaneous. These routes of administration and their particulars are well-known in the art of poultry vaccination.

If desired, subunit vaccines according to the invention are freeze-dried, in order to make them less dependent on cold storage.

Another, even more attractive vaccination-application is the use of live recombinant carrier virus (LRCV-) vaccines carrying a gene encoding a spike protein or an immunogenic fragment thereof comprising the receptor-binding domain, according to the invention Such live recombinant carrier viruses (LRCV's) are recombinant viruses capable of infecting a host animal, in this case poultry, and carrying a foreign gene under the control of a promoter. Such promoters may be promoters as discussed vide supra, and they may be viral promoters of the LRCV or heterologous viral promoters (vide infra).

The use of avian LRCV's as carriers for many different genes encoding viral or bacterial antigens is well-known in the art.

For the construction of most LRCV's, the well known technique of in vitro homologous recombination can be used to stably introduce a DNA molecule or plasmid according to the invention into the genome of an LRCV.

For RNA-based vectors such as Newcastle Disease virus, reverse genetics techniques have been described and are available.

Many avian vector viruses have been described in the literature, such as Marek's Disease type 1, 2 and 3, Fowl pox virus, Infectious Laryngotracheitis virus, Avian Adeno virus type 4 or 8 and avian paramyxovirus viruses such as Newcastle Disease virus.

Avian herpesviruses as a LRCV for the expression of heterologous antigen are described i.a. by Sondermeijer P. J., et al., in Vaccine. 11: 349-58 (1993) and in European Patent EP431668.

Examples of avian Herpesvirus are i.a. Marek's Disease virus type 1, 2 and 3 (type 3=Herpes virus of turkey).

The use of Infectious Laryngotracheitis virus as LRCV has been described i.a. in European Patent EP1241177.

The use of Newcastle Disease virus as a LRCV has been described e.g. in European Patent EP1996708.

Recombinant Newcastle Disease virus as a LRCV for avian influenza-H7 virus as a vaccine for protection of chickens against influenza and Newcastle disease has been described by Swayne, D. E. et al., in Avian Dis. 47: 1047-50 (2003).

Recombinant avian adenoviruses have i.a. been described in U.S. Pat. No. 6,296,852. Recombinant canary pox vectors are also known in the art as suitable LRCV's. They have been described for use in poultry and in non-avian species, i.a. by Taylor J, Meignier B, Tartaglia J, et al. (Vaccine 13: 539-549 (1995)).

One of the advantages of the use of avian LRCV is that they infect several cell types of poultry. In these cells, in the process of the replication of the virus, the foreign gene(s) that they carry, in this case the spike protein or a fragment thereof comprising the receptor-binding domain, according to the invention will also be expressed. As a result, trimeric or tetrameric spike proteins will be formed and secreted (or be exposed at the cell surface of the infected cells if they still comprise the trans membrane region). And this in turn will result in the induction of an appropriate immune response against the IBV spike in a form that at least closely resembles the native conformation of spike protein on the IB-virus. Therefore, the use of avian LRCV's would mimic the natural infection of cells with IBV.

Therefore, another embodiment of the present invention relates to a live recombinant carrier virus comprising a DNA molecule or a plasmid according to the invention.

In a preferred form of this embodiment, the live recombinant carrier virus according to the invention is selected from the group of Marek's Disease type 1, 2 and 3, Fowl pox virus, Infectious Laryngotracheitis virus, Avian Adeno virus and avian paramyxovirus.

A second advantage is that most LRCV's according to the invention can be administered e.g. through drinking water, aerosol and spray vaccination, or by eye drop, intratracheal or intranasal application. Especially the administration through drinking water, aerosol and spray vaccination allow for easy mass application of the vaccine.

Thus, although administration by injection, e.g. intramuscular or subcutaneous of LRCV-based vaccines according to the present invention is possible, such vaccines are preferably administered by the inexpensive mass application techniques commonly used for IBV vaccination. For IBV vaccination these techniques include drinking water, aerosol and spray vaccination. Alternatively, administration of the live vaccine can also be individually by eye drop, intratracheal or intranasal.

HVT is an exception to the rule, in the sense that HVT is administered best through injection, be it subcutaneous, intramuscular (i.m.) or in ovo.

The IBV vaccines according to the invention, both subunit and LRCV, can also be administered via the in ovo route. The in ovo administration of the vaccine involves the administration of the vaccine to an avian embryo while contained in the egg (for a review on in ovo vaccination see: Ricks et al., Advances in Vet. Med. 41, 495-515, 1999). The vaccine may be administered to any suitable compartment of the egg (e.g. allantois fluid, yolk sac, amnion, air cell or into the embryo) as described in the art (Sharma; Am. J. Vet. Res. 45, 1619-1623, 1984). Preferably the vaccine is administered below the shell (aircell) membrane and chorioallantoic membrane. Usually the vaccine is injected into embryonated eggs during late stages of the embryonation, generally during the final quarter of the incubation period, preferably 3-4 days prior to hatch. In chickens the vaccine is preferably administered between day 15-19 of the 21 day incubation period, in particular at day 17 or 18, most preferably at day 18 of the incubation period.

Thus, again another embodiment of the present invention relates to a vaccine for the protection of poultry against IBV infection, characterised in that said vaccine comprises an LRCV according to the invention and a pharmaceutically acceptable carrier.

It is clear that an amount of LRCV's should be administered that expresses sufficient IBV spike protein according to the invention to induce an immune response in chickens or turkeys that decreases the pathological effects of the disease, when compared to the pathological effects after infection with a wild-type IBV in non-immunized birds.

Typically, a LRCV-based vaccine according to the invention for both pre- and post-hatch administration comprises the LRCV according to the invention in a concentration of $10^{2.0}$-$10^{8.0}$ infectious particles per dose.

The exact dose is of course highly depending of the LRCV used. However, the skilled person would find ample guidance in the references above regarding LRCV's and their application in poultry.

The dose volume per bird depends on the route of vaccination and the age of the bird. Typically, eye drop vaccines are administered in a volume of 20-100 µl per dose at any age. Spray vaccines may contain the dose in a volume of 100-1000 µl for day-old birds and one dose of a drinking water vaccine usually is diluted in a volume of about 1 ml for each day of age.

A LRCV-based vaccine according to the invention for in ovo administration typically comprises an amount of the LRCV of $10^{2.0}$-$10^{8.0}$ infectious particles in a volume of 50-100 µl, preferably 50 µl.

Most of the LRCV-based vaccines according to the invention are sensitive to high temperatures, because they comprise live viruses. Thus, preferably, LRCV-based vaccines according to the invention should be freeze-dried, in order to make them less dependent on cold storage.

It is clear that buffers, stabilizers and the like as described above are suitable for use with LRCV-based vaccines, but of course, components that interfere with the viability of the live recombinant carrier viruses should be left out. In many cases, the use of an adjuvant can be omitted, because of the immunogenic nature of LRCV's.

Although subunit and LRCV-based IBV vaccines according to the present invention may be used effectively in chickens, also other poultry such as turkeys, pigeons, quail, pheasants, guinea fowl and partridges may be successfully vaccinated with the vaccine. The age of the birds receiving a subunit vaccine or an LRCV-based vaccine according to the invention after hatching is the same as that of the birds receiving the conventional commercially available live- or inactivated IBV vaccines. For example, broilers may be vaccinated pre-hatch as described (vide supra) or at one-day old or at 1-3 weeks of age, particularly for broilers with high levels of MDA. Laying stock or reproduction stock may also be vaccinated pre-hatch as described or initially at 1-10 days of age and boosted with a live or inactivated vaccine at 7-12 or 16-18 weeks of age.

An alternative and efficient way of vaccination is direct vaccination with a DNA molecule or plasmid according to the invention. Direct vaccination with DNA encoding proteins has been successful for many different proteins.

For mass application, this would in some cases not be the most attractive way of vaccination, because it would require injection of the DNA molecule. However, for applications that require administration by a needle anyway, such as in ovo vaccination against IBV infection, this way of vaccination is especially attractive, if only because it would avoid the use of LRCV's.

Thus, again another embodiment of the present invention relates to a vaccine for the protection of poultry against IBV infection, characterised in that said vaccine comprises a DNA molecule or plasmid according to the invention.

The amount of a DNA molecule or plasmid according to the invention, comprised in a pharmaceutical composition according to the invention can be in the broad range between 10 pg and 1000 µg. Preferably, amounts in the range between 0.1 and 100 µg are used.

A DNA molecule or plasmid according to the invention can be administered in a naked form or can be packaged in a delivery system. Suitable delivery systems are lipid vesicles, iscoms, dendromers, niosomes, polysaccharide matrices and the like, all well-known in the art.

Examples of standard text books giving further details on DNA vaccines and vaccination are 1) DNA Vaccines, Series: Methods in Molecular Medicine, Vol. 127 by Saltzman, Mark W.; Shen, Hong; Brandsma, Janet L. (Eds.) 2006, ISBN: 978-1-58829-484-5 and 2) DNA Vaccines, Methods and Protocols, Series: Methods in Molecular Medicine, Vol. 29, Lowrie, Douglas B.; Whalen, Robert (Eds.), 2000, ISBN: 978-0-89603-580-5.

Modern chicken farming can not rely on IBV-vaccines only. Several other vaccines for the protection of chickens against other chicken pathogens are administered, and most of these vaccines are administered at the same moment. Preferably, such vaccines are administered together in one shot as a combination vaccine.

Therefore, the invention also relates to combination vaccines for the protection of poultry against IBV that comprise, in addition to the subunit or LRCV according to the invention, an IBV vaccine capable of inducing protection against another IBV serotype and/or a vaccine capable of inducing protection in poultry against another avian pathogen.

Preferably, the combination vaccine comprises one or more vaccines selected from the group of Marek's Disease virus (MDV), Newcastle disease virus (NDV), infectious bursal disease virus (IBDV), egg drop syndrome (EDS) virus, turkey rhinotracheitis virus (TRTV), Reovirus or one or more vaccine strains of IBV.

It should be noted that an LRCV according to the present invention can be used for the vaccination of poultry, but also as a vector of expressing the IBV spike protein according to the invention in an in vitro cell system. Such cell systems are described above for the expression of the spike protein according to the invention.

Thus, another embodiment of the invention relates to a mammalian cell, characterised in that said mammalian cell comprises a DNA molecule according to the invention, a plasmid according to the invention, or a LRCV according to the invention.

EXAMPLES

Materials and Methods

Genes and Expression Vectors

IBV encoding sequences were obtained from the National Center for Biotechnology Information (NCBI) GenBank (http://www.ncbi.nlm nih gov/entrez/): IBV-M41 accession number AY851295, IBV-Beaudette CK accession number AJ311317, IBV-H120 accession number FJ888351, and IBV-B1648 accession number X87238. Human codon-optimized sequences of the S1 encoding domains (initiating directly downstream of the signal sequence till the furin cleavage site: IBV-M41, -Beaudette and -H120: aa19 to 532; IBV-B1648: a.a. 19-536) were synthesized (GenScript) and cloned into the pCD5 vector (Zeng et al., 2008). The S1 genes were preceded by a sequence encoding an N-terminal CD5 signal peptide and followed by sequences encoding a C-terminal artificial GCN4 trimerisation domain (GCN4; RMKQIEDKIEE-IESKQKKIENEIARIKKLVPRGSLE) (SEQ ID NO: 3) (Harbury et al., 1993) and the Strep-Tag II (ST; WSH-PQFEK (SEQ ID NO: 7), IBA GmbH) for affinity purification. Amino acid alignment of the IBV S1 domains was generated by Neighbor-Joining phylogeny and is depicted in FIG. 1A.

The full plasmid map of the construct pCD5-M41-S1-GCN4-ST is given in FIG. 6, the sequence of the plasmid is given in SEQ ID. 1.

Protein Expression and Purification

The pCD5 expression vectors containing the S1 domain-encoding sequences were transfected into HEK293T cells as previously described (Bosch et al., 2009; de Vries et al., 2010). Tissue culture supernatants were harvested 7 days post transfection. The S1 proteins were purified using Strep-Tactin sepharose beads according to the manufacturer's instructions (IBA GmbH). Similarly purified culture supernatants of HEK293T cells transfected with a pCD5 plasmid lacking the S1 coding sequence served as negative controls. When indicated, S1 proteins bound to Strep-Tactin beads were treated with *Vibrio Cholera* neuraminidase (Roche; 2 µU/ml) for 3 h at 37° C., followed by three washing steps prior to elution of the protein from the beads. The concentrations of the proteins were determined using the NanoDrop 1000 spectrophotometer (Thermo Fisher Scientific Inc) and confirmed by Western blot.

Western Blot

IBV S1 protein expression and purification was analyzed by SDS-PAGE followed by Western blotting using the HRPO-conjugated Strep-Tactin antibody (IBA GmbH). When indicated, the S1 proteins were treated with PNGaseF (New England Biolabs Inc.) prior to electrophoresis according to the manufacturer's procedures in order to remove N-linked oligosaccharides.

Spike Histochemistry

Formalin-fixed paraffin-embedded tissues from a 6-week-old male broiler chicken and from a male barnacle goose were sectioned at 4 um. Tissue sections were deparaffinized with xylene and rehydrated using graded alcohols. Antigen retrieval was performed by boiling in 10 mM sodium citrate (pH6.0) for 10 minutes in a microwave and subsequently the slides were washed three times in PBS. Endogenous peroxidase was inactivated by incubating the slides in 1% hydrogen peroxide in methanol for 30 min at RT, after which they were washed with PBS-0.1% Tween (TPBS) and blocked with 10% normal goat serum for 30 min. at RT. To detect S1 protein binding to avian tissues, protein (S1: 0.1 mg/ml) was pre-complexed with Strep-Tactin-HRPO (1:200, IBA GmbH) for 30 minutes on ice before applying them onto the slides. After overnight incubation at 4° C., the slides were rinsed three times in PBS and peroxidase was revealed with 3-amino-9-ethyl-carbazole (AEC, Sigma Aldrich). The tissues were counterstained with hematoxylin and mounted with Aquamount (Merck). To check for non-specific staining, slides were incubated with comparable volumes of similarly purified culture supernatants of HEK293T cells transfected with a pCD5 plasmid lacking the viral protein-encoding sequences. Images were captured using a CCD camera and Olympus BX41 microscope linked to a Cell'B imaging software (Soft Imaging Solutions GmbH, Germany).

The ability of *Maackia amurensis* (MAA) lectins to block the binding of S1 to the tissues was studied pre-incubating the slides with a concentration range (8-256 µg/ml) of non-conjugated MAAI and MAAII (Vector Laboratories Inc) overnight at 4° C., prior to performing spike histochemistry.

Lectin Histochemistry

Alpha-2,3-linked sialic acids were detected with lectins from *Maackia amurensis* (MAA). MAA I and MAAII labeled with biotin (Vector Laboratories Inc.) were applied to formalin-fixed paraffin-embedded tissues after antigen retrieval and endogenous peroxidase blocking as described for spike histochemistry. After blocking with 10% normal goat serum for 30 min at RT, 7 µg/ml lectins were applied to the slides and incubated overnight at 4° C. Next, the slides were washed three times in TPBS and subsequently incubated with peroxidase-conjugated avidin for 30 min using the Vector ABC kit (Vector Laboratories Inc). Peroxidase was revealed with AEC (Sigma Aldrich), and after counterstaining with hematoxylin the tissues were mounted with Aquamount (Merck). Images were captured using a CCD camera and Olympus BX41 microscope linked to a CellAB imaging software (Soft Imaging Solutions GmbH).

Results

Expression, Purification and Characterization of Soluble IBV S1 Proteins

In this study the binding characteristics of S1 proteins of four IBV strains with different pathogenicity profiles to avian tissues were compared. In particular, the research focused on the virulent Massachusetts reference strain M41 (Cavanagh, 1981), the life attenuated vaccine H120 strain (Bijlenga et al., 2004), the avirulent and cell culture-adapted Beaudette strain (Beaudette and Hudson, 1937), and the nephropathogenic B1648 strain (Pensaert et al., 1994; Meulemans et al., 2001), as representative examples of IBV strains with various pathogenicity. The S1 proteins of these IBV strains share 75-95% homology in amino acid sequence, however, pathogenicity profiles in vivo are marked different (summarized in FIG. 1A).

To allow their expression as soluble proteins, codon-optimized sequences of the S1 genes were cloned into the pCD5 expression vector, preceded by the CD5 signal peptide, and followed by sequences encoding the GCN4 trimerisation domain and the Strep-Tag II (FIG. 1B). Expression of the proteins was achieved by transfection of human HEK293T cells and proteins secreted into the medium were purified using the Strep-Tag technology (IBA, GmbH, Germany). The resulting proteins were analyzed by Western blot using the Strep-Tactin antibody either before or after PNGaseF treatment. The results show that all S1 proteins displayed a similar electrophoretic mobility, migrating around 105 kDa in SDS-PAGE (FIG. 1C). In all expression experiments the amount of Beaudette-S1 protein expressed and purified was less compared to the other S1 proteins, the reason for this remained unclear. PNGaseF treatment showed that, as expected (Yamada et al., 2009), the expressed S1 proteins were highly glycosylated (FIG. 1C). Removal of the N-linked glycans resulted in migration of the proteins around 70 kDa, which is somewhat slower than the predicted 65 kDa based on their amino acid sequence. In conclusion, soluble glycosylated S1 proteins of various IBV strains can be easily expressed and purified.

Specificity of Attachment of M41-S1 to the Avian Respiratory Tract and α-2,3-Linked Di-Sialoside.

The only host determinant yet identified to be involved in the infection of avian respiratory epithelium by IBV is alpha-2,3-linked sialic acid (Winter et al., 2008). Therefore, this study first compared the binding of S1 of the virulent reference strain IBV-M41 to the respiratory tract of chicken with that of *Maackiaa murensis* (MAA) lectins detecting α-2,3-sa. As differences in tissue distribution have been observed for different isoforms of MAA (Nicholls et al., 2007), both MAAI and MAAII were used in this study. Slides were prepared from formalin-fixed, paraffin embedded tissues from a 6-week-old broiler chicken and lectin- and spike binding was assessed by histochemistry.

In the trachea, M41-S1 bound to the cilia of epithelial cells as well as to goblet cells (FIG. 2A), in accordance with the reported sensitivity of those cells for IBV (Winter et al., 2008). No staining was observed when incubating slides with similarly purified culture supernatant of cells transfected with an empty vector (data not shown). For MAAI, binding to the cilia of the epithelial cell layer, as well as weak binding to the mucus-producing goblet cells was observed, while MAAII had a more profound affinity for the goblet cells of the trachea (FIG. 2A). Comparable results were observed using cryosections of tissues of the same animal (data not shown). A similar evaluation of binding to chicken lung tissue showed that M41-S1 primarily bound to the epithelial surface of the parabronchal area (FIG. 2B). Again, these data are in agreement with the reported sensitivity of bronchioepithelial cells for IBV (Abd El Rahman et al., 2010). Clear differences were observed between MAAI and MAAII binding to the lower respiratory tract. While MAAI preferentially bound to parabronchial epithelium, MAAII rather bound to connective tissue within the chicken lung. In conclusion, MAAI resembled the binding of M4'-S1 to chicken respiratory tract better than MAAII, confirming that these lectins have different specificities (Nicholls et al., 2007).

To investigate whether M41-S1 itself could serve as a lectin, subsequent blocking experiments were performed in which the slides were pre-incubated with MAAI before applying the M41-S1 protein. Binding of M41-S1 to the respiratory tract could be completely blocked by 64 µg/ml of MAAI (FIG. 2C). Interestingly, lower concentrations of MAAI only blocked M4'-S1 attachment to the goblet cells, but not to the epithelial cells of the trachea. In the lung, 8 µg/ml MAAI was already sufficient to completely block binding of M41-S1. These results demonstrate that M4'-S1 itself might serve as a lectin, and that it has marked preference for substrates recognized by MAAI. Furthermore, the differences in ability to block M41-S1 binding to particular cell types points towards affinity differences for various substrates present in these tissues.

Binding of M41-S1 to Goose Respiratory Tract

Next it was investigated whether the limited host tropism of IBV (that is, domestic fowl, but not other avian species are known to be susceptible to the virus) can be explained by the attachment pattern of IBV-S1 to the respiratory tract. To this end, the binding of M41-S1 to respiratory tissues of barnacle goose was investigated in a similar histochemistry assay. It was observed that M41-S1 was able to bind to goblet cells and mucus covering the epithelium of the goose trachea, however, no specific binding to the cilia of the epithelial cells was observed (FIG. 3). In the lung, no binding of M41-S1 to goose parabronchal epithelium was detected (FIG. 3), in contrast to that observed for chicken lung (FIG. 2B), although some staining of the goose primary bronchus was detected (not shown). To confirm the presence of α2,3-sa on goose tissues, MAAI and MAAII lectin histochemistry was performed, showing binding to cilia and goblet cells of the trachea and to parabronchi and air capillaries (FIG. 3). Taken together, these data suggest that binding of IBV-S1 to epithelial cells of the respiratory tract is predictive for the host species range and that the inability of IBV-M41 to infect goose can (at least partly) be explained by the restricted binding of the spike proteins to the goose respiratory epithelial cells.

S1 of Low Pathogenic IBV Strains have Reduced Binding Affinity for Chicken Tissues.

The binding characteristics of M41-S1 was compared with that of the S1 proteins of related, but avirulent, Massachusetts strains H120 and Beaudette. Both strains are generated by serial passage (for 120 and at least 250 times, respectively) in embryonated eggs and are considered non-pathogenic for chickens. That is, while H120 is a widely used vaccine strain (Bijlenga et al., 2004), Beaudette almost completely lost its capacity to replicate in vivo (Geilhausen et al., 1973). Spike histochemistry was performed by applying similar amounts of S1 proteins (5 µg per slide) onto sections of respiratory chicken tissue. It was observed that H120-S1 bound with much lower affinity to the trachea and the lung compared to M41-S1 (FIG. 4A). In particular, weak staining of the cilia, but no binding to goblet cells was observed in the trachea. In the lung, only minor staining of epithelial cells in the air capillaries could be detected. For Beaudette-S1 no binding to the respiratory tract could be detected at all (FIG. 4A), even with increasing amounts of protein (data not shown). In conclusion, these results show that the binding affinities of S1 correlate with the reported pathogenicity profiles of the respective IBVs in vivo.

As IBV has been isolated from the intestine (Raj and Jones, 1997) and sialic acids are abundantly present in the gut (Guo et al., 2007), the binding of S1 proteins to intestinal tissue was investigated. For both M41-S1 and H120-S1 mainly binding to mucus-producing goblet cells was observed (FIG. 4B). Strikingly, however, H120-S1 appeared to bind with higher affinity to these cells, as shown by the higher intensity of staining when using similar amounts of protein (5 µg per slide). Subsequent blocking experiments showed that MAAI was unable to block binding of M41-S1 and H120-S1 to goblet cells, even using concentrations up to 528 µg/ml (data not shown). Again, Beaudette-S1 was unable to bind to intestinal goblet cells at all.

Legend to the figures.

FIG. 1. Expression of recombinant IBV S1 proteins.

(A) Alignment of the S1 amino acid sequences of M41, H120, Beaudette and B1648. Indicated is the percentage of amino acid homology with the reference M41 strain and the reported pathogenicities; (B) Schematic representation of the S1 expression cassettes. The S1 ectodomain encoding sequence was cloned in frame with DNA sequences coding for a signal sequence, the GCN4 isoleucine zipper trimerisation motif, and the Strep-tag II under the control of a CMV promoter; (C) S1 proteins expressed in HEK293T cells and purified from the culture media were analyzed by SDS-PAGE followed by Western blot using the Streptactin; when indicated the samples were treated with PNGaseF prior to electrophoresis.

Figure 2:
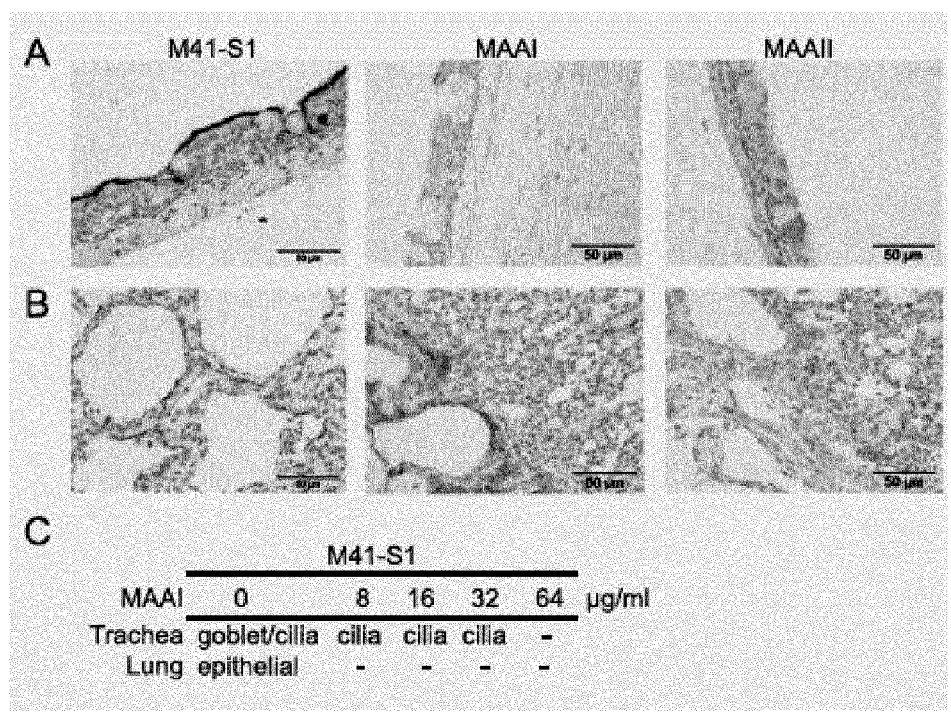
Figure 3:
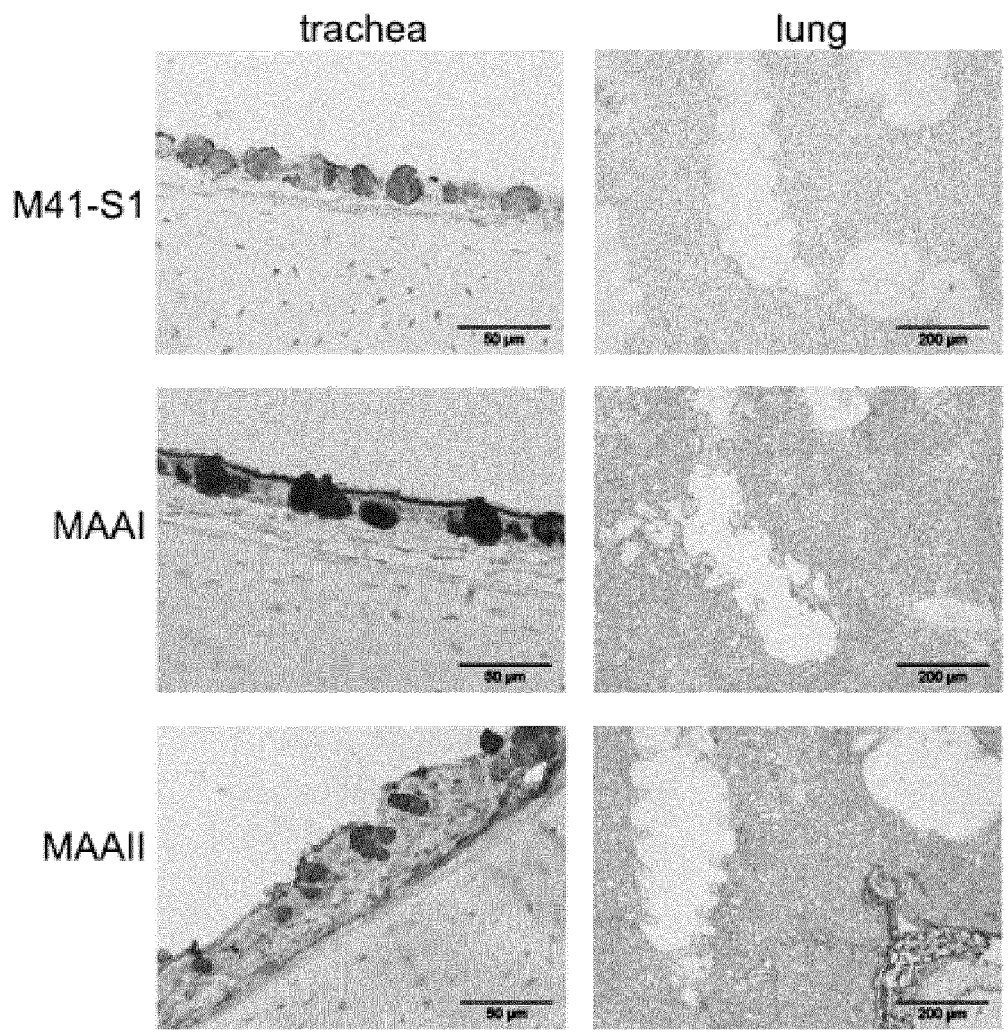

FIG. 2. Attachment pattern of M41-S1 to chicken respiratory tissues.

Tissue slides were analyzed for binding of recombinant M41-S1. Spike—and lectin histochemistry were performed by incubating chicken trachea (A) or chicken lung (B) slides with precomplexed Streptactin-M41-S1 or with biotynylated lectins MAAI and MAAII; (C) Tissue slides of trachea and lung were pretreated with the indicated concentrations of non-biotynylated MAAI or MAAI and subsequently used for spike histochemistry;

(−): not detectable.

FIG. 3. M41-S1 binding characteristics to goose respiratory tract

Barnacle goose trachea and lung tissue slides were used for histochemistry with M41-S1. Lectins MAAI and MAAII served as controls on the goose tissue to demonstrate the presence of a2,3-sialic acids.

Figure 4:
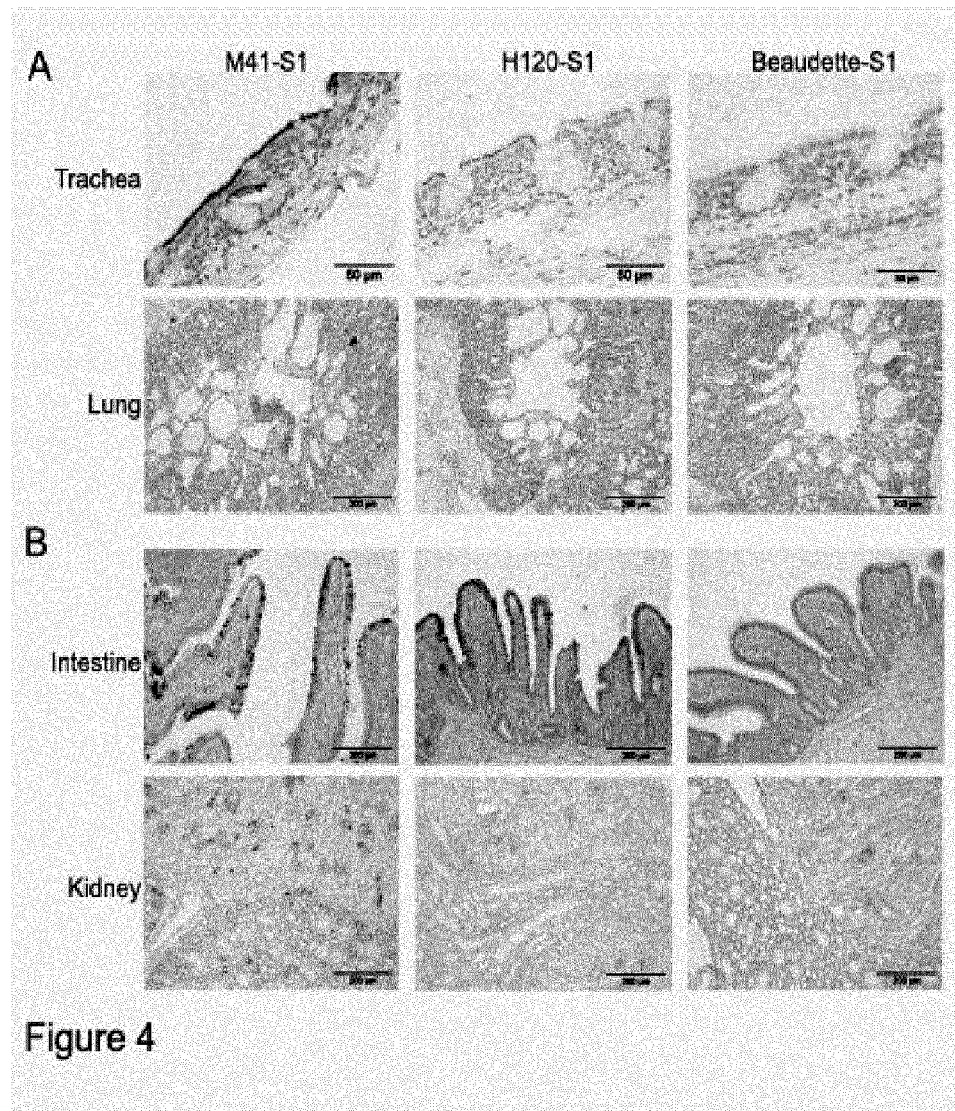

FIG. 4. Spike histochemistry of S1 proteins of IBV strains with various pathogenicity Spike histochemistry was performed with similar amounts of precomplexed M41-S1, H120-S1 and Beaudette-S1 using tissue slides of chicken (A) trachea, lung, (B) intestine and kidney.

FIG. 5. Spike histochemistry using recombinantly expressed spike proteins of IBV-M41 on chicken respiratory tract tissue.

Spike histochemistry was performed with dimeric S1 protein and trimeric S1 protein on chicken trachea and lung tissue.

FIG. 6. full plasmid map of the construct pCD5-M4'-S1-GCN4-ST.

REFERENCES

Abd El Rahman, S., C. Winter, A. El-Kenawy, U. Neumann, and G. Herrler. 2010. Differential sensitivity of well-differentiated avian respiratory epithelial cells to infection by different strains of infectious bronchitis virus. J. Virol. 84:8949-8952.

Bosch, B. J., R. Bodewes, R. P. de Vries, J. H. Kreijtz, W. Bartelink, G. van Amerongen, G. F. Rimmelzwaan, C. A. de Haan, A. D. Osterhaus, and P. J. Rottier. 2010. Recombinant Soluble, Multimeric HA and NA Exhibit Distinctive Types of Protection against Pandemic Swine-Origin 2009 A(H1N1) Influenza Virus Infection in Ferrets. J. Virol. 84:10366-10374.

Beaudette, F. R., and C. B. Hudson. 1937. Cultivation of the virus of infectious bronchitis.

Bijlenga, G., J. K. Cook, J. Gelb Jr, and J. J. de Wit. 2004. Development and use of the H strain of avian infectious bronchitis virus from the Netherlands as a vaccine: a review. Avian Pathol. 33:550-557.

Cavanagh, D. 1981. Structural polypeptides of coronavirus IBV. J Gen Virol. 53:93-103.

de Vries, R. P., E. de Vries, B. J. Bosch, R. J. de Groot, P. J. Rottier, and C. A. de Haan. 2010. The influenza A virus hemagglutinin glycosylation state affects receptor-binding specificity. Virology. 403:17-25.

Geilhausen, H. E., F. B. Ligon, and P. D. Lukert. 1973. The pathogenesis of virulent and avirulent avian infectious bronchitis virus. Arch. Gesamte Virusforsch. 40:285-290.

Guo, C. T., N. Takahashi, H. Yagi, K. Kato, T. Takahashi, S. Q. Yi, Y. Chen, T. Ito, K. Otsuki, H. Kida, Y. Kawaoka, K. I. Hidari, D. Miyamoto, T. Suzuki, and Y. Suzuki. 2007. The quail and chicken intestine have sialyl-galactose sugar chains responsible for the binding of influenza A viruses to human type receptors. Glycobiology. 17:713-724.

Harbury, P. B., T. Zhang, P. S. Kim, and T. Alber. 1993. A switch between two-, three-, and four-stranded coiled coils in GCN4 leucine zipper mutants. Science. 262:1401-1407.

Meulemans, G., M. Boschmans, M. Decaesstecker, T. P. Berg, P. Denis, and D. Cavanagh. 2001. Epidemiology of infectious bronchitis virus in Belgian broilers: a retrospective study, 1986 to 1995. Avian Pathol. 30:411-21.

Nicholls, J. M., A. J. Bourne, H. Chen, Y. Guan, and J. S. Peiris. 2007. Sialic acid receptor detection in the human respiratory tract: evidence for widespread distribution of potential binding sites for human and avian influenza viruses. Respir. Res. 8:73.

Pensaert, M., and C. Lambrechts. 1994. Vaccination of chickens against a Belgian nephropathogenic strain of infectious bronchitis virus B1648 using attenuated homologous and heterologous strains. Avian Pathol. 23:631-641.

Raj, G. D., and R. C. Jones. 1997. Infectious bronchitis virus: Immunopathogenesis of infection in the chicken. Avian Pathol. 26:677-706.

Yamada, Y., and D. X. Liu. 2009. Proteolytic activation of the spike protein at a novel RRRR/S motif is implicated in furin-dependent entry, syncytium formation, and infectivity of coronavirus infectious bronchitis virus in cultured cells. J Virol. 83:8744-58.

Winter, C., G. Herrler, and U. Neumann. 2008. Infection of the tracheal epithelium by infectious bronchitis virus is sialic acid dependent. Microbes Infect. 10:367-73.

Zeng, Q., M. A. Langereis, A. L. van Vliet, E. G. Huizing a, and R. J. de Groot. 2008. Structure of coronavirus hemagglutinin-esterase offers insight into corona and influenza virus evolution. Proc. Natl. Acad. Sci. U.S.A. 105:9065-9069.

The invention claimed is:

1. An infectious bronchitis virus (IBV) spike protein or an immunogenic fragment thereof comprising a receptor-binding domain, wherein said spike protein consists of an IBV S1 protein or an immunogenic fragment thereof of the IBV S1 protein; and wherein said IBV spike protein or said immunogenic fragment thereof is C-terminally fused to a trimerisation or tetramerisation domain that is not a coronaviral heptad repeat.

2. The IBV spike protein or an immunogenic fragment thereof of claim 1, characterised in that said spike protein is an IBV spike protein of the IBV Massachusetts serotype.

3. The IBV spike protein or an immunogenic fragment thereof of claim 1, characterised in that said spike protein is an IBV spike protein of the IBV 793B serotype.

4. A trimeric or tetrameric spike protein structure of infectious bronchitis virus (IBV) spike protein or an immunogenic fragment thereof comprising a receptor-binding domain of claim 1.

5. A DNA molecule that encodes an IBV spike protein or an immunogenic fragment thereof of claim 1.

6. A plasmid characterised in that said plasmid comprises a DNA molecule encoding an IBV spike protein or an immunogenic fragment thereof, according to claim 5 under the control of a promoter.

7. An Avian Live Recombinant Carrier Virus (LRCV), characterised in that said LRCV comprises the DNA molecule of claim 5 or a plasm id comprising said DNA molecule under the control of a promoter.

8. The LRCV according to claim 7, wherein said virus is selected from the group of Marek's Disease type 1, 2 and 3, Fowl pox virus, Infectious Laryngotracheitis virus, Avian Adeno virus and Avian Paramyxovirus.

9. A subunit vaccine for the protection of poultry against IBV infection, characterised in that said vaccine comprises an immunogenic amount of an IBV spike protein or an immunogenic fragment thereof, of claim 1 and a pharmaceutically acceptable carrier.

10. The subunit vaccine according to claim 9, characterised in that said vaccine comprises an adjuvant.

11. A vaccine for the protection of poultry against IBV infection, characterised in that said vaccine comprises an LRCV according to claim 7, and a pharmaceutically acceptable carrier.

12. A combination vaccine for the protection of poultry against IBV infection, characterised in that said vaccine comprises a vaccine according to claim 11, and an IBV vaccine capable of inducing protection against another IBV serotype and/or a vaccine capable of inducing protection against another avian pathogen.

13. A combination vaccine for the protection of poultry against IBV infection according to claim 12, characterised in that said vaccine capable of inducing protection against another avian pathogen is selected from the group of vaccines that protects against Marek's Disease virus (MDV), Newcastle disease virus (NDV), infectious bursal disease virus (IBDV), egg drop syndrome (EDS) virus, turkey rhinotracheitis virus (TRTV), Reovirus or one or more vaccine strains of IBV.

14. A mammalian cell, that comprises a DNA molecule according to claim 5.

15. The DNA molecule of claim 5 that encodes an IBV spike protein selected from the group consisting of the IBV Massachusetts serotype, the IBV 793B serotype, an immunogenic fragment of the IBV Massachusetts serotype, or an immunogenic fragment of the IBV 793B serotype.

16. A plasmid comprising the DNA molecule of claim 15 under the control of a promoter.

17. An Avian Live Recombinant Carrier Virus (LRCV), characterised in that said LRCV comprises the DNA molecule of claim 15 or a plasmid comprising said DNA molecule under the control of a promoter.

18. The LRCV according to claim 17, wherein said virus is selected from the group of Marek's Disease type 1, 2 and 3, Fowl pox virus, Infectious Laryngotracheitis virus, Avian Adeno virus and Avian Paramyxovirus.

19. A vaccine for the protection of poultry against IBV infection, characterised in that said vaccine comprises an LRCV of claim 18, and a pharmaceutically acceptable carrier.

20. A vaccine for the protection of poultry against IBV infection, characterised in that said vaccine comprises an LRCV of claim 17, and a pharmaceutically acceptable carrier.

* * * * *